United States Patent [19]

Buren et al.

[11] Patent Number: 4,595,411

[45] Date of Patent: Jun. 17, 1986

[54] METHOD OF INCREASING THE YIELD OF PLANTS UTILIZING N-(2'-DIETHYLAMINOETHYL)ALKYLAMIDES

[75] Inventors: Lawrence L. Buren, Cupertino; Don R. Baker, Orinda, both of Calif.

[73] Assignee: Stauffer Chemical Co., Westport, Conn.

[21] Appl. No.: 707,999

[22] Filed: Mar. 4, 1985

Related U.S. Application Data

[63] Continuation-in-part of Ser. No. 495,191, May 16, 1983, abandoned.

[51] Int. Cl.⁴ .................. A01N 37/18; A01N 37/22
[52] U.S. Cl. ........................................ 71/118
[58] Field of Search .............. 71/106, 113, 118, 77; 564/207, 215

[56] References Cited

U.S. PATENT DOCUMENTS 4,148,926  4/1979  Baker et al. .................... 426/333
4,218,234  8/1980  Nadasy et al. .................... 71/86

OTHER PUBLICATIONS

Shibata et al., "Plant Growth Regulators", Chem. Abs. 90:67737, (1979).

*Primary Examiner*—Glennon H. Hollrah
*Assistant Examiner*—R. Lelkes
*Attorney, Agent, or Firm*—M. J. Bradley

[57] ABSTRACT

A method of increasing the yield of plants utilizing a compound of the formula

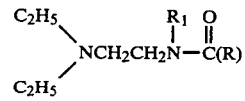

wherein R is $C_3$–$C_{14}$ alkyl or $C_3$–$C_6$ alkenyl and $R_1$ is hydrogen, $C_1$–$C_3$ alkyl or phenyl.

14 Claims, No Drawings

METHOD OF INCREASING THE YIELD OF PLANTS UTILIZING N-(2'-DIETHYLAMINOETHYL)ALKYLAMIDES

CROSS REFERENCE TO RELATED APPLICATIONS

This application is a continuation-in-part of application Ser. No. 495,191, filed May 16, 1983 now abandoned.

BRIEF DESCRIPTION OF THE INVENTION

The present invention provides a compound and a method by which the yield of certain plants, particularly crop plants, can be improved by applying to such plants a yield-improving amount of N-(2'-diethylaminoethyl) alkylamide. The plants for which the present invention has been found especially useful are the monocots, such as corn and wheat, and dicots, such as cotton, tobacco and sunflower.

The application of N-(2'-diethylaminoethyl) alkylamide improves the yield of corn, sunflower and cotton as much as 28, 20, and 176 percent, respectively. Total dry matter of the entire above-ground portion of the plant was increased also. The term "yield" includes but is not restricted to weight and chemical compounds of any or all plant parts. Methods for the production of N-(2'-diethylaminoethyl) alkylamides, the compound and use of the compound N-(2'-diethylaminoethyl) alkylamides as an anti-ripening agent were disclosed in U.S. Pat. No. 4,148,926, issued Apr. 10, 1979.

DESCRIPTION OF THE INVENTION

The compounds that are useful in the practice of this invention are N-(2'-diethylaminoethyl) alkylamides having the structural formula

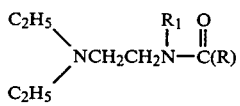

wherein R is $C_3$-$C_{14}$ alkyl or $C_3$-$C_6$ alkenyl and $R_1$ is hydrogen, $C_1$-$C_3$ alkyl or phenyl.

The compounds useful in the invention, N-(2'-diethylaminoethyl) alkylamides can be prepared by the general method of reacting the diethylaminoethylamine with the appropriate acid chloride using a suitable acid binding agent in a neutral solvent. The compounds where $R_1$ is hydrogen can also be prepared by reaction of the appropriate ester with N,N-diethyl ethylene diamine.

Example 1 below teaches the method of preparation and application as disclosed below.

EXAMPLE 1

Preparation of N-(2'-diethylaminoethyl) Undecamide

First, 7.0 milliliters (ml) (0.05 mole) N,N-diethylethylenediamine, 50 ml methylene chloride, and 5.2 ml (0.065 mole) pyridine were combined in a flask. Next, 13 ml (0.06 mole) undecanyl chloride was added at −60° C. with stirring. The temperature was allowed to rise to 0° C. The reaction mixture was then washed two times with 300 ml portions of water and a 100 ml portion of saturated sodium carbonate solution. The organic solution was dried over magnesium nitrate and then stripped in vacuum to yield 9.7 g of the desired product, $n_D^{30}$ 1.4556. This compound will be referred to as Compound No. 1.

TABLE I

| Compound Number | R | $R_1$ | $n_D^{30}$ melting point |
|---|---|---|---|
| 1 | —$(CH_2)_9CH_3$ | H | 1.4556 |
| 2 | —$C(CH_3)_3$ | H | 1.4421 |
| 3 | —$C(CH_3)$=$CH_2$ | —phenyl | 1.4934 |
| 4 | —$(CH_2)_{10}CH_3$ | H | low melting material |
| 5 | —$(CH_2)_8CH_3$ | H | 1.4582 |
| 6 | —$(CH_2)_6CH_3$ | H | 1.4585 |
| 7 | —$(CH_2)_6CH_3$ | —$CH_2CH_3$ | 1.4531 |

EVALUATION TEST ON CORN

The purpose of this test was to evaluate Compound No. 1 for corn seed and corn plant dry weight increase. The compound of this invention was evaluated for such weight increase in the following manner.

Round fiber pots [8 inches (20.32 cm) in diameter and 8 (20.32 cm) inches tall] were filled with screened, sandy loam soil which had been fortified with 17-17-17 granular fertilizer to yield a soil mix having 150 parts per million (ppm) each of nitrogen, $P_2O_5$ and $K_2O$. Approximately ten corn seeds (DeKalb XL45A) were planted in the soil about 0.5 inches deep in a single row. Eleven days after seeding the plants were thinned to two per pot and nineteen days after seeding the plants were thinned to one plant per pot.

Several such pots are retained as controls and other pots are treated with the candidate compound. The time of treatment of the plants was 13 and 19 days after planting. The plants were treated with the compound by spraying one milliliter of 10, 20 or 30 ppm solution on the plants in each pot. These applications approximate 0.0133, 0.0267 or 0.0400 pounds per acre (lb/A) (14.90, 29.90 or 44.80 grams per hectare). The compound was dissolved in a 1:1 acetone-$H_2O$ mixture containing 0.5 percent polyoxyethylene sorbitan monolaurate emulsifier prior to the treatment. Each treatment was replicated seven times.

The treated plants were grown outdoors for the duration of the experiment. The plants were fertilized three times during the crop cycle with 1:1:1 ratio of a nitrogen, $P_2O_5$, $K_2O$ fertilizer solution (3.4 grams nitrogen, $P_2O_5$, $K_2O$ per liter of water). Seventy milliliters of this solution was added to each pot at each of the three fertilization times.

Control plants were fertilized and maintained in a like manner but were not treated with the candidate compound.

When the plants had fully matured, the ears were removed from the plants and stalk height was determined. The plants were severed at the soil surface and the tops and ears were dried in a forced-air dryer at 120° F. to a constant weight, i.e., until all moisture was evaporated from the tissues. Next, the dry weight of the tops and the corn seed which had been ascertained individually were compared to the corresponding dry weights of the untreated plants.

Corn seed oil was analyzed by use of a Newport Analyzer Mark IIIA NMR using procedures established by the manufacturer. A 40 ml sample assembly is used for soybeans and sunflower samples. Samples were analyzed at room temperature using an RF level of 224 uA and an integration time of 32 seconds. Gate width used was 1 gauss. The NMR analyzer was standardized by use of a FGIS sealed sunflower seed standard. Variable weight samples were used (weights were recorded to the nearest 0.01 gram). Oil content of the sunflower seed samples was calculated with the following formula:

$$\text{Constant} = \frac{\text{NMR reading of calibration standard}}{(\text{weight of seed}) \times (\text{soil content of standard})}$$

$$\% \text{ Oil} = \frac{\text{NMR reading of seed sample}}{(\text{weight of samples}) \times (\text{constant})}$$

The constant used for all seed samples was 0.2562. The oil content of the corn samples was calculated as above using a correction factor of 1.054 times the NMR reading of the sample.

The mean percent increase in dry weight over the control was calculated and is reported in Table II. Control weights and percents were as follows: seed dry weight—84.2 g/plant; and total (tops and ears) dry weight—183.3 g/plant; and corn seed oil—24.34%.

TABLE II

| Treatment Rate ppm | Mean Percent Increase | | |
|---|---|---|---|
| | Seed Dry Weight | Total (tops & ears) Dry Weight | Corn Seed Oil |
| 10 | 23.6 | 14.2 | 1.1 |
| 20 | 27.5 | 15.2 | 2.8 |
| 30 | 24.4 | 16.5 | 3.6 |

EVALUATION TEST ON SUNFLOWER

The purpose of this test was to evaluate Compound No. 1 for sunflower seed and sunflower plant dry weight increases. The compound of this invention was evaluated for such weight increase in the following manner.

Round fiber pots [8 inches (20.32 cm) in diameter and 8 inches (20.32 cm) tall] were filled with screened, sandy loam soil which had been fortified with 17-17-17 granule fertilizer to yield a soil mix having 150 ppm each of nitrogen, $P_2O_5$ and $K_2O$. Approximately eight sunflower seeds (Primasoul) were planted in each pot in a single row. Eight days after planting the plants were thinned to one plant per pot.

Eight days after seeding the plants were taken from the greenhouse, treated and then moved outdoors for the duration of the test. The plants were treated by spraying one milliliter of a 10, 50, 90 or 130 ppm solution on the plant in each pot. The treatment applications were repeated 7 days layer. These applications approximate 0.0133, 0.0666, 0.1198 or 0.1732 pounds per acre (lb/a) (14.90, 74.48, 136.06 or 193.65 grams per hectare). The compound was dissolved in a 1:1 acetone-$H_2O$ mixture containing 0.5% polyoxyethylene sorbitan monolaurate emulsifier prior to the treatment. Each treatment was replicated five times.

The plants were fertilized three times during the crop cycle with a 1:1:1 ratio of a nitrogen, $P_2O_5$, $K_2O$ fertilizer solution (3.4 grams nitrogen, $P_2O_5$, $K_2O$ per liter of solution). Seventh milliliters of this solution was added to each pot at each of three fertilization times.

Control plants were fertilized and maintained in a like manner but were not treated with the candidate compound.

When the plants were fully mature, measurements were made on total plant (above-ground portions) dry weight and seed dry weight. The seed head was removed from the plant and then the plant was severed at the soil level. The plants and seedheads were dried in a forced-air dryer at 120° F. to a constant weight, i.e., until all moisture was evaporated from the plant tissues. The seeds were removed from the seedheads and then the seed dry weight and the total plant (excluding the seed) dry weight were determined on an individual basis. The weights obtained for the treated plants were compared to those of the untreated plants.

The mean percent increase in dry weight over the control was calculated and is reported in Table III.

TABLE III

| Treatment Rate ppm | Mean Percent Increase | |
|---|---|---|
| | Seed Dry Weight | Total Plant (veg. + seed) Dry Weight |
| 10 | 1.3 | 2.5 |
| 50 | 8.2 | 9.7 |
| 90 | 19.6 | 18.0 |
| 130 | 8.2 | 7.5 |

EVALUATION TEST ON COTTON

The purpose of this test was to evaluate Compound No. 1 for cotton production and cotton plant dry weight increase. The compound of this invention was evaluated for such weight increase in the following manner.

Round fiber pots [8 inches (20.32 cm) in diameter by 8 inches (20.32 cm) tall] were filled with screened, sandy loam soil which had been fortified with 17-17-17 granular fertilizer to yield a soil mix having 150 ppm each of nitrogen, $P_2O_5$, and $K_2O$. Approximately eight cotton seeds (Acala SJ-2) were planted in each pot in a single row. Seventeen days after planting the plants were thinned to one plant per pot.

At 7, 17 and 52 days after seeding the plants were taken from the greenhouse, treated and then placed back into the greenhouse for the duration of the test. The plants were treated by spraying 2, 2, or 5 ml (at 7, 17 and 52 days, respectively) of a 75, 125 or 175 ppm solution on the plant in each pot. These applications approximate 0.1500, 0.2500 and 0.3500 lb/A (168, 280 and 392 grams per hectare). The compound was dissolved in a 1:1 acetone-$H_2O$ mixture containing 0.5% polyoxyethylene sorbitan monolaurate emulsifier prior to the treatment. Each treatment was replicated eight times.

The plants were fertilized three times during the crop cycle with a 1:1:1 ratio of a nitrogen, $P_2O_5$, $K_2O$ fertilizer solution (3.4 grams of nitrogen, $P_2O_5$, $K_2O$ per liter of solution). Seventy milliliters of this solution was added to each pot at each of three fertilization times.

Control plants were fertilized and maintained in a like manner but were not treated with the candidate compound.

Approximately 2 weeks prior to boll opening of the most mature bolls, the bolls were counted and removed from the plants and the above-ground portion of the plants were collected for drying. The plants and bolls were dried in a forced-air dryer at 120° F. to a constant weight, i.e., until all of the moisture was evaporated from the tissues. Then the dry weights were obtained individually for the bolls and for the remainder of the plant. The weights and boll counts for the treated plants were compared to those of the untreated plants. The mean percent increase for each parameter over the control was calculated and is reported in Table IV.

TABLE IV

| Treatment Rate ppm | Mean Percent Increase | | | |
|---|---|---|---|---|
| | Boll | | | Total Plant (veg. + bolls) D.W. |
| | No. | Mean D.W. | Total D.W. | |
| 75 | 46 | 52 | 122 | 48 |
| 125 | 62 | 43 | 131 | 44 |
| 175 | 62 | 71 | 176 | 60 |

EVALUATION OF COMPOUND 1 ON TOBACCO (COKER 48)

Tobacco plants were grown in round fiber pots (6" dia.×6" tall) in the greenhouse. The pots were filled with screened sandy loam soil. Prior to spraying the plants were thinned to one per pot.

The plants were sprayed with 80 GPA of the appropriate spray solution 32 and 39 days after planting. The chemicals were dissolved in a 1:1 acetone/water mixture containing 0.5% Tween 20 ® (polyoxyethylene sorbitan monolaurate emulsifier). Treatments were replicated six times.

The plants were harvested approximately 2 months after planting. They were divided into leaves and stems and the dried in a forced-air dryer and weighed separately.

TABLE V

| Treatment Rate lb/Acre | Mean Percent Increase | | |
|---|---|---|---|
| | Stem | Leaves | Total |
| 0.00375 | 102 | 40 | 51 |
| 0.0075 | 37 | 9 | 14 |
| 0.015 | 86 | 52 | 58 |
| 0.03 | 107 | 41 | 53 |
| 0.06 | 69 | 23 | 31 |

EVALUATION TEST ON CORN

The purpose of this test was to evaluate the compounds for corn seed and/or seedling dry weight increase. The compounds of this invention was evaluated for such weight increase in the following manner.

Round fiber pots [8 inches (20.32 cm) in diameter and 8 (20.32 cm) inches tall] were filled with screened, sandy loam soil which had been fortified with 17-17-17 granular fertilizer to yield a soil mix having 150 parts per million (ppm) each of nitrogen, $P_2O_5$ and $K_2O$. Approximately ten Goldcrest corn seeds (Compounds 1-5) or Illini corn seeds (Compounds 6 and 7) were planted in the soil about 0.5 inches deep in a single row. Eleven days after seeding the plants were thinned to four per pot and nineteen days after seeding the plants were thinned to one plant per pot. The three seedlings removed from each pot in the test using Illini corn were dried in a forced-air dryer to constant weight and then weighed.

Several such pots are retained as controls and other pots are treated with the candidate compound. The time of treatment of the plants was 13 and 19 days after planting. The plants were treated with the compound by spraying one milliliter of 30 ppm solution on the plants in each pot. These applications approximate 0.0400 pounds per acre (lb/A) (44.80 grams per hectare). The compound was dissolved in a 1:1 acetone-$H_2O$ mixture containing 0.5 percent polyoxyethylene sorbitan monolaurate emulsifier prior to the treatment. Each treatment was replicated seven times.

The treated plants were grown outdoors for the duration of the experiment. The plants were fertilized three times during the crop cycle with 1:1:1 ratio of a nitrogen, $P_2O_5$, $K_2O$ fertilizer solution (3.4 grams nitrogen, $P_2O_5$, $K_2O$ per liter of water). Seventy milliliters of this solution was added to each pot at each of the three fertilization times.

Control plants were fertilized and maintained in a like manner but were not treated with the candidate compound.

When the plants had fully matured, the ears were removed from the plants and were dried in a forced-air dryer at 120° F. to a constant weight, i.e., until all moisture was evaporated from the tissues.

The mean percent increase in seedling and/or seed dry weight over the control was calculated and is reported in Table VI.

TABLE VI

| Compound Number | Mean Percent Increase | |
|---|---|---|
| | Seed Dry Weight | Seeling Dry Weight |
| 1 | 73 | — |
| 2 | 149 | — |
| 3 | 77 | — |
| 4 | 152 | — |
| 5 | 76 | — |
| 6 | 37 | 27 |
| 7 | 3 | 22 |

EVALUATION OF COMPOUND 4 ON WINTER WHEAT

Round fiber pots (12" dia.×8" tall) were filled with a sandy loam soil that had been screened and fortified with a granular 17-17-17 fertilizer. Enough fertilizer was added to equal 150 ppm each of N, $P_2O_5$ and $K_2O$ in the final mix. Approximately 20 wheat seeds were planted into each pot in a single row. Two weeks after planting the plants were thinned to twelve plants per pot. The pots were kept in the greenhouse for two days after the first spraying. The remainder of the time they were outdoors.

The plants were sprayed 16 days and approximately 10 weeks after planting with 80 GPA of the appropriate spray solutions. The solutions were prepared by dissolving the appropriate amount of chemical in 1:9 acetone/water mixture containing 0.5% Tween 20 ® (polyoxyethylene sorbitan monolaurate emulsifier) or water containing 0.5% Tween 20 ®. The plants were in the early two-leaf (first spraying) and five-leaf stage with profuse tillering (second spraying). The treatments were replicated five times. All treatments were uniformly fertilized ten weeks after planting. At harvest the heads were clipped, counted, dried in a forced-air dryer and weighed.

TABLE VII

| Treatment Rate lb/Acre | Mean Percent Increase in Dry Weight of Heads |
|---|---|
| 0.00375 | 10.5 |
| 0.0075 | −3.3 |

TABLE VII-continued

| Treatment Rate lb/Acre | Mean Percent Increase in Dry Weight of Heads |
|---|---|
| 0.015 | 31.8 |
| 0.03 | 29.2 |
| 0.06 | 8.7 |

Application of N-(2'-diethylaminoethyl) alkylamide may be made employing the procedures normally used for treatment of plants including dip or soak treatment of seeds, tubers, bulbs or cuttings, for example, as well as foliar, bark or stem or soil application. Preferably the compounds are applied in a postemergence foliar application, more preferably the compounds are applied directly to the plant between plant emergence and about 3 weeks after flowering of the plant. The active ingredient may be utilized in diverse formulations, including the adjuvants and carriers normally employed for facilitating the dispersions of active ingredients for agricultural applications, recognizing the known fact that the formulations and mode of application of a chemical agent may affect its activity in any given application. Thus, N-(2'-diethylaminoethyl) alkylamide can be formulated as a solution or dispersion in a non-aqueous medium, as a powdery dust, as a wettable powder, as an emulsifiable concentrate, as a granule or as any of several other known types of formulations, depending upon the desired mode of application. These growth regulatory compositions may be applied as dusts, sprays, dips or granules in the sites in which growth regulation is desired. These formulations may contain as little as 0.0005% or as much as 95% or more by weight of active ingredients and applications may be at rates of between about 1/300th to about 5 pounds per acre, preferably between about 1/100th to about 2 pounds per acre.

Dusts are admixtures of the active ingredient with finely divided solids such as talc, attapulgite clay, kieselguhr and other organic and inorganic solids which act as dispersants and carriers for the regulant. These finely divided solids have an average particle size of less than 50 microns. A typical dust formulation useful herein is one containing 1.0 part of N-(2'-diethylaminoethyl) alkylamide and 99.0 parts of talc.

Wettable powders are in the form of finely divided particles which disperse readily in water or other dispersant. The wettable powder is ultimately applied to the plant either as a dry dust or as an emulsion in water or other liquid. Typical carriers for wettable powders include fuller's earth, kaolin clays, silicas, and other highly absorbent, wettable inorganic diluents. Wettable powders normally are prepared to contain about 5% to 80% of active ingredient, depending upon the absorbency of the carrier and usually also contain a small amount of a wetting, dispersing or emulsifying agent to facilitate dispersion.

Other useful formulations for plant applications are the emulsifiable concentrates which are homogeneous liquid or paste compositions which are dispersable in water or other dispersant and may consist entirely of N-(2'-diethylaminoethyl) alkylamide with a liquid or solid or emulsifying agent or may also contain a liquid carrier such as xylene, heavy aromatic naphthas, isophorone and other nonvolatile organic solvents. For plant application, these concentrations are dispersed in water or other liquid carrier and normally applied as a spray to the area to be treated. The percentage of weight of the essential active ingredient may vary according to the manner in which the composition is to be applied, but in general, comprises 0.0005% to 95% of active ingredient.

Other useful formulations include simple solutions of the active ingredient in a dispersant in which it is completely soluble at the desired concentration, such as acetone or other organic solvents. Granular formulations wherein the chemical agent is carried on relatively coarse particles are of particular utility for aerial distribution or for penetration of cover crop canopy. Pressurized sprays, typically aerosols wherein the active ingredient is dispersed in finely-divided form as a result of vaporization of low boiling dispersant solvent carrier such as the freons, may also be used.

Of course, the formulations, concentration and mode of application of N-(2'-diethylaminoethyl) alkylamide will be adapted to the particular plant and surrounding circumstances as is the case in all agronomic applications.

The active growth regulatory compounds of this invention may be formulated and/or applied with other agricultural chemicals, such as herbicides, insecticides, fungicides, nematocides, fertilizers and the like. In addition, combinations of N-(2'-diethylaminoethyl) alkylamide with certain plant hormones, such as native auxins, antiauxins, gibberellins and kinins, may produce enhanced growth regulatory effects.

What is claimed is:

1. A method of increasing the yield of plants comprising applying thereto a yield-increasing amount of a compound having the formula

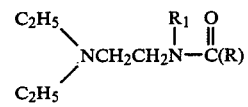

wherein R is $C_3$–$C_{14}$ alkyl or $C_3$–$C_6$ alkenyl and $R_1$ is hydrogen, $C_1$–$C_3$ alkyl or phenyl.

2. The method of claim 1 wherein the yield-increasing amount of said compound is between about 1/300th to about 5 pounds per acre.

3. The method of claim 1 wherein the yield-increasing amount is applied between plant emergence and 8 weeks after flowering.

4. The method of claim 1 wherein the yield-increasing amount of said compound is between about 1/100th to about 2 pounds per acre.

5. The method of claim 3 wherein the yield-increasing amount of said compound is between about 1/100th to about 2 pounds per acre.

6. The method of claim 1 wherein the plants are selected from the group consisting of monocots and dicots.

7. The method of claim 1 wherein the plants are crops selected from the group consisting of corn, wheat, cotton, tobacco and sunflowers.

8. The method of claim 1 wherein R is —$(CH_2)_9CH_3$ and $R_1$ is hydrogen.

9. The method of claim 1 wherein R is —$C(CH_3)_3$ and $R_1$ is hydrogen.

10. The method of claim 1 wherein R is

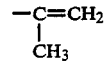

and $R_1$ is phenyl.

11. The method of claim 1 wherein R is —$(CH_2)_{10}CH_3$ and $R_1$ is hydrogen.

12. The method of claim 1 wherein R is —$(CH_2)_8CH_3$ and $R_1$ is hydrogen.

13. The method of claim 1 wherein R is —$(CH_2)_6CH_3$ and $R_1$ is hydrogen.

14. The method of claim 1 wherein R is —$(CH_2)_6CH_3$ and $R_1$ is —$CH_2CH_3$.

* * * * *

UNITED STATES PATENT AND TRADEMARK OFFICE
CERTIFICATE OF CORRECTION

PATENT NO. : 4,595,411

DATED : June 17, 1986

INVENTOR(S) : L. L. Buren et al.

It is certified that error appears in the above-identified patent and that said Letters Patent is hereby corrected as shown below:

In Column 1, line 26, "...and chemical compounds of" should read ..."and chemical components of".

In Column 3, line 7, ..."RF level of 224" should read ..."RF level of 225"

In Column 3, line 59, ..."repeated 7 days layer." should read ..."repeated 7 days later."

Signed and Sealed this

Twenty-third Day of December, 1986

*Attest:*

DONALD J. QUIGG

*Attesting Officer*     *Commissioner of Patents and Trademarks*